United States Patent

Pies et al.

[11] Patent Number: 5,466,881
[45] Date of Patent: Nov. 14, 1995

[54] PROCESS FOR PREPARING M-CHLOROAROMATICS

[75] Inventors: Michael Pies, Duisburg; Helmut Fiege, Leverkusen; Lothar Puppe, Burscheid; Josef Käsbauer, Wermelskirchen, all of Germany

[73] Assignee: Bayer Aktiengesellschaft, Leverkusen, Germany

[21] Appl. No.: 232,550

[22] Filed: Apr. 22, 1994

[30] Foreign Application Priority Data

Apr. 30, 1993 [DE] Germany .................. 43 14 299.0

[51] Int. Cl.⁶ .................. C07C 17/00; C07C 25/00
[52] U.S. Cl. ....................... 570/202; 570/190
[58] Field of Search ....................... 570/202, 190

[56] References Cited

U.S. PATENT DOCUMENTS 4,368,339  1/1983  Tada et al. .................. 570/202
4,650,915  3/1987  Arpe et al. .
4,935,561  6/1990  Eichler et al. .

FOREIGN PATENT DOCUMENTS 0046665   3/1982   European Pat. Off. .
0072008   2/1983   European Pat. Off. .
0278729   8/1988   European Pat. Off. .
3420706  12/1985   Germany ............... 568/202

*Primary Examiner*—Werren B. Lone
*Attorney, Agent, or Firm*—William C. Gerstenzang; Sprung Horn Kramer & Woods

[57] ABSTRACT

In the preparation of m-chloroaromatics by isomerizing corresponding o- and/or p-chloroaromatics in the liquid phase over zeolites, the activity of the zeolites remains at a high level for a particularly long time if the process is carried out in the presence of from 1 to 30 mol % of hydrogen, based on the chloroaromatics used.

8 Claims, No Drawings

PROCESS FOR PREPARING M-CHLOROAROMATICS

The present invention relates to a particularly advantageous process for preparing m-chloroaromatics by isomerizing corresponding o- and/or p-chloroaromatics over zeolites.

Dichlorobenzene and chlorotoluene are generally prepared by chlorination of monochlorobenzene and toluene respectively. This results, depending on the reaction conditions and catalysts used, in isomer mixtures having different compositions being obtained, these mixtures containing o-, m- and p-dichlorobenzene or o-, m- and p-chlorotoluene. However, each m-isomer is always present in very small amounts in such mixtures (see Ullmanns Encyclopedia of Industrial Chemistry, 5th edition, volume A6, pages 333 ff.). However, for some applications, for example for the preparation of intermediates for crop protection agents and medicaments, mainly m-dichlorobenzene and m-chlorotoluene are required.

Processes for preparing m-dichlorobenzene and m-chlorotoluene, in which the corresponding o- and/or p-compounds are isomerized, have therefore been disclosed. Such processes which are of particular interest are those using zeolites as isomerization catalysts, since they are processwise and ecologically advantageous (see, for example, DE-A 33 34 673, DE-A 34 20 706, EP-A 46 665 and JP Application No. 57-27 279=JP Offenlegungsschrift 58-144 330). However, this process has the disadvantage that the zeolites have to be regenerated within time periods of at most about 200 hours.

This also applies to processes in which addition of hydrogen to the chloroaromatics to be isomerized is possible. Thus, DE-A 33 34 673 describes a process for preparing m-dichlorobenzene by isomerization of o- and/or p-dichlorobenzene, in which diluents, such as nitrogen or hydrogen, may optionally be added to lower the partial pressure of the dichlorobenzenes when working in the gas phase (see page 6, lines 4 to 7). Specifically, an addition of 4 and 5.35 moles of nitrogen per mole of dichlorobenzenes used is described (see Examples 1 and 4). No statement is made about the time periods after which the zeolite catalysts have to be regenerated.

DE-A 34 20 706 describes a process for isomerizing 2-, 3- and/or 4-chlorotoluene over zirconium-containing zeolites which are said to excel by combining a long operating time with particularly high activity. The process can be carried out in the gaseous or liquid phase and hydrogen can optionally be admixed with the starting material, for example in amounts of 880 mol %, based on 2-chlorotoluene. The activity and selectivity of the catalyst is maintained for 210 hours (see Example 1b). In processes which had hitherto become known, catalyst deactivation takes place in significantly shorter time periods (see page 4, lines 9 to 12).

Finally, EP-A 46 665 discloses an isomerization process for halogenated toluenes, in which acid zeolites are used as catalysts. According to the description, the process can optionally be carried out in the presence of hydrogen (see page 4, lines 14 to 16). However, in Example 1, the only example with addition of gas, 5 mol of nitrogen are used per mole of o-chlorotoluene/chlorobenzene mixture. There are no quantitative data about the time periods after which the catalysts have to be regenerated.

There is therefore still a need for an isomerization process for preparing m-chloroaromatics in which a high catalyst activity is maintained over time periods of more than about 200 hours, so as to reduce the need for regeneration of the catalysts.

A process has now been found for preparing m-chloroaromatics of the formula (I)

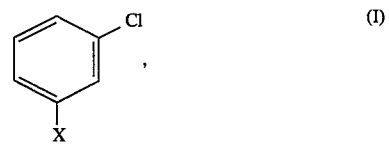

in which
X represents methyl or chlorine,
by isomerizing o- and/or p-chloroaromatics of the formulae (IIa) and (IIb)

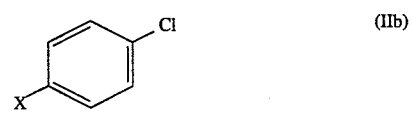

in which
X represents methyl or chlorine,
which is characterized in that o- and/or p-chloroaromatics of the formulae (IIa) and (IIb) are brought into contact with zeolites at elevated temperature in the liquid phase and in the presence of from 1 to 30 mol % of hydrogen, based on the chloroaromatics used.

In the process of the invention, technical grade o- or p-dichlorobenzene or technical grade o- or p-chlorotoluene or any desired mixtures containing o- and/or p-dichlorobenzene and/or o- and/or p-chlorotoluenes can be used. Preference is given to using mixtures as are obtained in the dichlorination of benzene or the monochlorination of toluene or in the workup of such chlorination mixtures, for example in workup by fractional distillation and/or fractional crystallization. Such mixtures can, for example, besides o- and/or p-dichlorobenzene or o- and/or p-chlorotoluene, optionally contain amounts of starting materials for the chlorination, i.e. benzene or toluene, of less chlorinated products, i.e. monochlorobenzene, of more highly chlorinated products, i.e. for example tri- and tetrachlorobenzene or for example di- and trichlorotoluene, and already, for example, up to a maximum of 20% by weight of m-dichlorobenzene or, for example, up to a maximum of 15% by weight of m-chlorotoluene. Preferably the chloroaromatics used contain less than 8% by weight of the respective m-isomer.

For the process of the invention, the source of the chloroaromatics or the chloroaromatic mixtures and their o- and/or p-isomer contents are of no particular importance.

Suitable temperatures for the process of the invention are, for example, those in the range from 150 to 500° C. The process is preferably carried out at from 200 to 450° C. The pressure at the respective temperature should be selected so as to be at least high enough for the chloroaromatics used to be present essentially in the liquid phase. This means that, even at reaction temperatures of less than 200° C. increased pressure is necessary. Suitable pressures can lie, depending on the reaction temperature used, for example, in the range from 1 to 100 bar. Preferably they lie in the range from 10 to 50 bar.

Suitable reactors are, for example, pressure-resistant reaction tubes which are filled with pelletized zeolites or zeolite granules.

The construction material of the reactor is preferably nickel or tantalum or an alloy with a high content of these metals, for example according to DIN 17742 (1963) No. 24602. Not suitable are materials with high contents of iron.

It is an essential feature of the present invention that the process is carried out in the presence of from 1 to 30 mol % of hydrogen, based on the chloroaromatics used. Preferably this amount is from 3 to 10 mol %, particularly from 3.5 to 8 mol %. Excessive amounts of hydrogen should be avoided, since these have a negative effect on the residence time over the zeolite catalyst and the isomerization can no longer take place virtually completely in the liquid phase.

In the process of the invention, various zeolites can be used as catalysts, for example those of the pentasil, mordenite and/or faujasite type. Preference is given to using ZSM-5 zeolites of the pentasil type, particularly preferably ZSM-5 zeolites in the H form.

It is advantageous to use the zeolite in granulated form, for example in the form of particles having an average particle diameter from 1 to 8 mm. Optionally, the zeolites may contain conventional binders.

The process of the invention can, for example, be carried out in such a way that the weight hourly space velocity over the zeolites is from 0.05 to 5 $h^{-1}$. Preferably the weight hourly space velocity is selected so as to be in the range from 0.07 to 5 $h^{-1}$, particularly preferably in the range from 0.1 to 2.5 $h^{-1}$.

If the o- and/or p-chloroaromatics to be used in the process of the invention contain interfering impurities in solid and/or dissolved form, it is advantageous to purify these chloroaromatics, for example, by filtration and/or treatment with siliceous earth, bleaching earth or similar agents, prior to them being brought into contact with zeolites.

With the process of the invention it is possible to keep zeolite catalysts in the isomerization of o- and p-chloroaromatics at high activities over longer time periods. For economic reasons, it is then frequently no longer practical to regenerate the zeolites, but rather to use a fresh batch. By this means the frequency and duration of interruptions to production is brought to a very much lower level than was hitherto considered possible.

It is extremely surprising that this increase in operating time of zeolites in the isomerization of o- and p-chloroaromatics in the liquid phase can be achieved with such small additions of hydrogen. Hitherto, consideration was given only to hydrogen additions, if any, of a number of moles per mole of starting material, and operating times of at most about 200 hours were achieved. A relationship between operating time and addition of hydrogen has hitherto not been recognized. The method of the invention enables operating times of, for example, from 1,000 to 1,500 hours with good activity to be realized. Any reduction in activity which may then be observed can be compensated by a small increased in the reaction temperature, for example by from 5° to 20° C. (see Example 2).

EXAMPLES

Example 1

A mixture of 34% by weight of o-, 2% by weight of m- and 58.2% by weight of p-dichlorobenzene and 5.3% by weight of trichlorobenzenes was isomerized over H-ZSM-5 zeolite with addition of 5 mol % of hydrogen, based on the total of dichlorobenzenes.

The reaction was carried out in the liquid phase at 350° C. and 30 bar and a weight hourly space velocity of 0.1 per hour.

The composition of the reaction product was analysed by gas chromatography after 24 hours and then approximately every 100 further hours. Details are given in Table 1.

From this it can be seen that after almost 1,000 hours the isomerized mixture contained a practically unchanged high proportion (40% by weight) of m-dichlorobenzene. This corresponds to a catalyst lifetime which is at least approximately 5 times longer than the longest catalyst lifetime which has hitherto become known.

Comparative Example 1

The procedure was as in Example 1, but without adding any hydrogen. Details are likewise given in Table 1. From this it can be seen that in the absence of hydrogen the catalyst activity has already fallen by over 20% after approximately 230 hours.

In Table 1, the column "m-dichlorobenzene content" gives the % by weight of m-dichlorobenzene which was contained in the reaction mixture after the time indicated in each case.

Example 2

The procedure was as described in Example 1, but using another batch of H-ZSM-5 zeolite and carrying out the reaction for 1,500 hours. After an operating time of 1,450 hours the temperature was increased to 360° C. Details are given in Table 1. Even after 1,500 hours, an isomer mixture containing over 40% by weight of m-dichlorobenzene was (again) obtained.

TABLE 1

| Example 1 | | Comparative Example 1 | | Example 2 | |
|---|---|---|---|---|---|
| Time (h) | m-dichloro-benzene content (%) | Time (h) | m-dichloro-benzene content (%) | Time (h) | m-dichloro-benzene content (%) |
| 24 | 42.5 | 27 | 42.2 | 31 | 45.9 |
| 121 | 42.8 | 70 | 42 | 122 | 45.8 |
| 214 | 42.0 | 179 | 37.9 | 196 | 43.7 |
| 312 | 40.6 | 191 | 35.9 | 349 | 42.6 |
| 408 | 41.1 | 233 | 33.3 | 415 | 39.6 |
| 504 | 41.1 | | | 504 | 40.3 |
| 611 | 40.1 | | | 595 | 39.9 |
| 699 | 39.0 | | | 665 | 39.5 |
| 815 | 38.3 | | | 780 | 39.4 |
| 914 | 39.4 | | | 871 | 39.5 |
| 986 | 40.0 | | | 986 | 39.5 |
| | | | | 1,114 | 38.2 |
| | | | | 1,210 | 37 |
| | | | | 1,409* | 35.9 |
| | | | | 1,501 | 41.1 |

*after 1450 hours the temperature was increased to 360° C.

Example 3

The procedure was as in Example 1, but working at 300° C. and isomerizing pure o-chlorotoluene. Details are summarized in Table 2. From this it can be seen that after more than 600 hours the reaction mixture contained a practically unchanged proportion of m-chlorotoluene.

According to the prior art (DE-A 34 20 706), the reaction product contains, despite continually increasing temperature, only 16.4% by weight of m-chlorotoluene after 210 hours (see Table 1 therein, selectivity for 3-chlorotoluene in relation to conversion of 2-chlorotoluene).

TABLE 2

| | Example 3 | |
|---|---|---|
| Time (h) | | m-chlorotoluene content (%) |
| 48 | | 27.6 |
| 116 | | 28.9 |
| 199 | | 29.1 |
| 311 | | 29.9 |
| 403 | | 28.1 |
| 500 | | 29.2 |
| 613 | | 29.1 |

What is claimed is:

1. A process for preparing m-chloroaromatics of the formula (I)

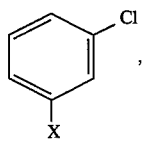  (I)

in which

X represents methyl or chlorine, by isomerizing o-chloroaromatics of the formulae (IIa) or p-chloroaromatics of the formula (IIb)

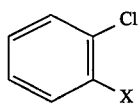  (IIa)

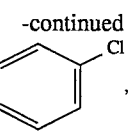  (IIb)

or a mixture thereof, in which

X represents methyl or chlorine, comprising that o-chloroaromatics, p-chloroaromatics or said mixtures thereof are brought into contact with a zeolite at elevated temperature in the liquid phase and in the presence of from 1 to 30 mol % of hydrogen, based on the chloroaromatics used.

2. The process of claim 1, comprising that technical grade o- or p-dichlorobenzene or technical grade o- or p-chlorotoluene or any desired mixture thereof is used.

3. The process of claim 1, comprising that it is carried out at a temperature in the range from 150° to 500° C. and at a pressure at which the chloroaromatics used are present essentially in the liquid phase.

4. The process of claim 1, comprising that it is carried out at a pressure in the range from 10 to 100 bar.

5. The process of claim 1, comprising that it is carried out in the presence of from 3 to 10 mol % of hydrogen, based on the chloroaromatics used.

6. The process of claim 1, comprising that the zeolite used is of the pentasil, mordenite or faujasite type.

7. The process of claim 1, comprising that a ZSM-5 zeolite in the H form is used.

8. The process of claim 1, comprising that it is carried out at a weight hourly space velocity over the zeolite in the range from 0.05 to 5 $h^{-1}$.

* * * * *

UNITED STATES PATENT AND TRADEMARK OFFICE
CERTIFICATE OF CORRECTION

PATENT NO. : 5,466,881
DATED     : November 14, 1995
INVENTOR(S): Pies, et al.

It is certified that error appears in the above-indentified patent and that said Letters Patent is hereby corrected as shown below:

Col. 6, line 10   After " that " insert -- said --

Signed and Sealed this

Twenty-eighth Day of May, 1996

Attest:

BRUCE LEHMAN

Attesting Officer        Commissioner of Patents and Trademarks